United States Patent [19]

Toyoshima et al.

[11] Patent Number: 4,920,180
[45] Date of Patent: Apr. 24, 1990

[54] HIGHLY WATER-ABSORPTIVE OCULAR LENS MATERIAL

[75] Inventors: Nobuyuki Toyoshima; Takanori Shibata; Atsushi Hirashima, all of Nagoya, Japan

[73] Assignee: Menicon Co., Ltd., Nagoya, Japan

[21] Appl. No.: 320,598

[22] Filed: Mar. 8, 1989

[30] Foreign Application Priority Data

Mar. 9, 1988 [JP] Japan .................................. 62-55708
Dec. 10, 1988 [JP] Japan ............................... 62-312719

[51] Int. Cl.$^5$ ...................... C08F 216/12; C08F 16/12
[52] U.S. Cl. ............................. 525/328.9; 525/329.5; 525/330.6; 526/329.6; 526/329.5
[58] Field of Search .................. 525/330.6, 283, 329.5, 525/328.9; 526/329.5, 329.6

[56] References Cited

U.S. PATENT DOCUMENTS

| | | | |
|---|---|---|---|
| 4,665,123 | 5/1987 | Gallanberg | 525/59 |
| 4,727,097 | 2/1988 | Kobayashi et al. | 525/283 |
| 4,745,158 | 5/1988 | Nakashima et al. | 525/276 |

*Primary Examiner*—Joseph L. Schofer
*Assistant Examiner*—T. McDonald, Jr.
*Attorney, Agent, or Firm*—Oblon, Spivak, McClelland, Maier & Neustadt

[57] ABSTRACT

A highly water-absorptive ocular lens material obtained by saponification for hydrophilic treatment of a copolymer composed essentially of:

(A) from 2 to 30 parts by weight of a (meth)acrylate polymer having at least one polymerizable group per molecule on an average obtained by copolymerizing (a) an alkyl (meth)acrylate monomer and (b) a monomer having at least two polymerizable groups per molecule, as the main components;

(B) from 70 to 98% by weight of a fatty acid vinyl ester; and (C) from 0.02 to 3.0 parts by weight of a cross linking agent, provided that the total amount of polymer (A) and monomer (B) is 100 parts by weight.

12 Claims, No Drawings

HIGHLY WATER-ABSORPTIVE OCULAR LENS MATERIAL

The present invention relates to a highly water-absorptive ocular lens material. More particularly, it relates to a highly water-absorptive ocular lens material suitable for use as a material for contact lenses, intraocular lenses or artificial cornea.

An attention has been drawn to a substance-permeable material as the application of polymer materials to the field of medical materials has been advanced. In particular, an attention has been drawn to a gas-permeable material for an optical material for medical applications, such as a contact lens material and an artificial cornea material.

Among various requirements for the contact lens material, the gas permeability, particularly, the oxygen permeability, is one of the most important requirements. Because, it is necessary to supply an adequate amount of oxygen through the contact lens material to the cornea so that the metabolic function of the corneal tissues will not be hindered.

In order to improve the gas permeability, the following methods have been proposed.

(1) A method in which a material known to have excellent gas permeability, such as a silicone rubber material, is employed as the contact lens material.

(2) A method wherein a copolymer composed essentially of a silicon containing monomer known as a gas-permeable monomer, such as a siloxanylalkyl (meth)acrylate monomer, is used as the contact lens material.

(3) A method wherein the water-content of the material itself is increased so that the gas-permeability is improved by utilizing the behavior of water contained in the material.

The method (1) has a difficulty relating to the water repellency inherent to the silicone rubber material. For instance, when used as a contact lens material, it exhibits poor affinity to the corneal surface or to tears, and lipophilic stains are likely to adhere on its surface, whereby it is likely to give a damage to the corneal tissues, or the lens material is likely to have white turbidity.

According to the method (2), it is possible to obtain a material having excellent gas-permeablility. However, such a material is hard material in most cases. Therefore, when used as a contact lens, it tends to give an uncomfortable feeling to the wearer, or it is likely to give a damage to the corneal tissues.

According to the method (3), the material softens upon absorption of water, whereby it gives a comfortable feeling to the wearer, and it is possible to increase the gas-permeability by increasing the water content.

Many of such highly water-absorptive material have excellent permeability for a gas such as oxygen by means of water absorbed in the material. Therefore, when used as contact lenses, they are capable of supplying an adequate amount of oxygen physiologically required for the cornea, from the atmosphere to the cornea by means of the water contained in the material, and thus they are highly safe to the eyes from the physiological viewpoint.

While such materials have excellent properties as mentioned above, they have difficulties in that since they have a high water content, the mechanical strength upon absorption of water is extremely low, and when formed into shaped products, they are susceptible to breakage, and thus have a problem in the durability.

In the field of medical materials, an attempt has been made to obtain a mechanically reinforced material by the copolymerization of a hydrophilic monomer such as vinyl pyrrolidone and a polymer having polymerizable groups, as essential components, in order to solve the problem in the durability, particularly the problem in the mechanical strength, while satisfying the high water-absorptive property.

The material composed essentially of vinyl pyrrolidone can be made to have a high water content at a level of about 80%. However, if the water content approaches to the level of about 80%, the mechanical strength tends to be still low and the durability is no still satisfactory for use as an ocular lens material. Thus, there still remains the problem unsolved.

On the other hand, Japanese Examined Patent Publications Nos. 49222/1982 and 15647/1985 disclose materials composed essentially of polyvinyl alcohols.

Japanese Examined Patent Publication No. 49222/1982 is concerned with a shaped product for medical use made of a modified polyvinyl alcohol obtained by copolymerizing a vinyl ester with a hydrophobic monomer having a high molecular weight at a level of from 1,000 to 10,000 and containing a polymerizable double bond at its terminal, followed by saponification.

Japanese Examined Patent Publication No. 15647/1985 is concerned with a process for producing a chemically-bonded, phase-separated and spontaneously cured hydrophilic thermoplastic graft copolymer obtained by copolymerizing a hydrophobic polymerizable monomer having a large molecular weight (linear polymer) with at least one hydrophilic copolymerizable comonomer.

However, in the materials disclosed in the above two publications, a high molecular weight hydrophobic monomer or linear polymer (hereinafter referred to as a "macromonomer") having a polymerizable double bond only at one terminal end of the polymer chain, is employed, and if such a macromonomer is polymerized with a vinyl eser or with a hydrophilic copolymerizable comonomer, the resulting copolymer will contain a substantial amount of the non-polymerized macromonomer since the macromonomer has a low concentration of polymerizable groups, and if the non polymerized macromonomer is not adequately removed by purification, a macro phase-separation is likely to occur in the material upon absorption of water, whereby it is likely that a transparent material is hardly obtainable, although the mechanical strength may be improved to some extent by the physical cross linking owing to intertwining of the copolymer chains to one another. Further, in such polymerization, no susbstantial chemical cross linking takes place, whereby there will remain various problems with respect to the dimensional stability, the insolubility (solvent resistance) against various solvents, the durability such as boiling resistance for heat sterilization, etc.

For such reasons, the materials made of such macromonomers are not suitable for use as ocular lens materials for medical applications. Further, Japanese Examined Patent Publication No. 49222/1982 discloses no specific application to ocular lens material.

Furthermore, the macromonomers disclosed in the above two publications, are prepared by living anion polymerization, whereby the operation for this polymerization reaction is cumbersome, and the production efficiency of such macromonomers is very poor. Therefore, it is extremely difficult to produce the material inexpensively in a large amount on an industrial scale.

Under the circumstances, it has been desired to develop a highly water-absorptive ocular lens material which has a high water content at a level of about 70% higher and which, nevertheless, has excellent transparency and satisfactory mechanical strength, dimensional stability, solvent resistance, boiling resistance, durability and productivity.

Proposed as a material excellent in the above-mentioned various properties is a highly water absorptive optical material obtained by saponification of a copolymer of a (meth)acrylate polymer and a fatty acid vinyl ester as main components (Japanese Unexamined Patent Publication No. 21101/1987).

However, such an optical material still contains a certain amount of a linear chain polyvinyl alcohol which is not chemically bonded to the (meth)acrylate polymer, and there still remains a problem that such a linear chain polyvinyl alcohol elutes to a certain extent. Since the linear chain polyvinyl alcohol has a high molecular weight, it takes time for elution from the material. In order to let the material pass the elution test for medical equipments (the difference in the amount of consumption of potassium permanganate) as stipulated by Ministry of Health and Welfare in Japan, long post treatment i.e. continuous boiling for at least 36 hours used to be required. (According to the regulation by the Ministry of Health and Welfare, the amount of elution of low molecular weight polymers, monomers or other organic substances contained in the material for medical equipments such as contact lenses is stipulated simply as the difference in the amount of consumption of potassium permanganate.)

Under these circumstances, the present inventors have conducted extensive researches with an aim to provide a highly water absorptive ocular lens material suitable for medical applications, particularly for ocular lenses, which is superior to the conventional highly water absorptive materials in the high water absorptivity, gas permeability and transparency and yet has the required durability such as mechanical strength, dimensional stability and solvent resistance and which contains little substances to be eluted and can meet the standard of the elution test for medical equipments as stipulated by the Ministry of Health and Welfare by the post treatment (i.e. extraction treatment by boiling) for a relatively short period of time. As a result, they have found an ocular lens material which has such various physical properties, and the present invention has been accomplished on the basis of this discovery.

The present invention provides a highly water-absorptive ocular lens material obtained by saponification for hydrophilic treatment of a copolymer composed essentially of:

(A) from 2 to 30 parts by weight of a (meth)acrylate polymer having at least one polymerizable group per molecule on an average obtained by copolymerizing (a) an alkyl (meth)acrylate monomer and (b) a monomer having at least two polymerizable groups per molecule, as the main components;

(B) from 70 to 98% by weight of a fatty acid vinyl ester; and (C) from 0.02 to 3.0 parts by weight of a cross linking agent, provided that the total amount of polymer (A) and monomer (B) is 100 parts by weight.

The (meth)acrylate polymer as defined above under (A) may hereinafter be referred to simply as the polymer (A). Likewise, the fatty acid vinyl ester under (B) may hereinafter be referred to simply as the monomer (B). In this specification, the term "(meth)acrylate" represents an acrylate and a methacrylate. Likewise, the term "(meth)acrylic acid" represents acrylic acid and methacrylic acid.

The highly water-absorptive ocular lens material can be obtained by a hydrophilic treatment by saponification of the copolymer composed essentially of:

(A) from 2 to 30 parts by weight of a (meth)acrylate polymer having at least one polymerizable group per molecule on an average obtained by copolymerizing (a) an alkyl (meth)acrylate monomer and (b) a monomer having at least two polymerizable groups per molecule, as the main components (the polymer (A));

(B) from 70 to 98% by weight of a fatty acid vinyl ester (the monomer (B)); and (C) from 0.02 to 3.0 parts by weight of a cross linking agent (hereinafter referred to as the cross linking agent (C)).

In the present invention, the cross linking agent (C) is incorporated when the above-mentioned polymer (A) and monomer (B) are copolymerized. Therefore, a linear chain polyvinyl alcohol which is not chemically bonded and elutable, will thereby be chemically bonded in the material. As the result, no substantial elution of the polyvinyl alcohol is observed. Therefore, the post treatment can be completed in an extremely short period of time. Further, the mechanical strength of the material and the durability such as dimensional stability, boiling resistance or solvent resistance, are improved since the polyvinyl alcohol is chemically bonded in the material.

The polymer (A) in the present invention contains at least one polymerizable group per molecule on an average, and thus is efficiently copolymerizable with a monomer having a polymerizable group, such as the monomer (B). Especially, when the polymer (A) has at least two polymerizable groups, chemical cross linking will be formed by the copolymerization with a monomer having a polymerizable group, such as the monomer (B), and the number of chemical cross linking sites increases with an increase of the number of polymerizable groups, whereby it is possible to obtain an optical material which undergoes no macro phase-separation upon absorption of water and which has excellent transparency and durability such as mechanical strength, solvent resistance, dimensional stability and boiling resistance.

The polymer (A) can readily be obtained by copolymerizing an alkyl (meth)acrylate monomer (hereinafter refered to simply as a component (a)) and a monomer having at least two polymerizable groups per molecule (hereinafter referred to simply as a component (b)), as the main components.

The component (a) is an alkyl (meth)acrylate monomer in which the alkyl group is a straight chain, branched chain or cyclic alkyl group or such an alkyl group with hydrogen atoms substituted by halogen atoms such as fluorine. Specific examples of the component (a) include alkyl (meth)acrylates such as methyl (meth)acrylate, ethyl (meth)acrylate, propyl (meth)acrylate, butyl (meth)acrylate, pentyl (meth)acrylate, hexyl (meth)acrylate, dodecyl (meth)acrylate, cyclohexyl (meth)acrylate, trifluorethyl (meth)acrylate, pentafluoropropyl (meth)acrylate and hexafluoroisopropyl (meth)acrylate. These monomers may be used alone or in combination as a mixture of two or more different kinds.

As the component (a), it is preferred to employ a lower alkyl (meth)acrylate, for example, one having from 1 to 6 carbon atoms, since it is thereby possible to conduct the copolymerization of the polymer (A made of such a component (a) with a monomer having a polymerizable group, such as the monomer (B), without bringing about a steric hindrance.

Specific examples of the component (b) include monomers having at least two polymerizable groups per molecule, such as allyl (meth)acrylate, vinyl (meth)acrylate, ethylene glycol di(meth)acrylate, diethylene glycol di(meth)acrylate, triethylene glycol di(meth)acrylate and dipropylene glycol di(meth)acrylate. These monomers may be used alone or in combination as a mixture of two or more different kinds.

It is preferred to suitably select the component (b) by taking into consideration the copolymerizability of the polymerizable group of the polymer (A) made of the component (b) with the polymerizable group of the other copolymerizable monomer such as the monomer (B). Because, for instance, the copolymerizability differs between a vinyl group and a (meth)acryloyl group or between an allyl group and a (meth)acryloyl group, and if such polymerizable groups having different copolymerizability are copolymerized, the copolymerization will be incomplete, thus leading to phase-separation, whereby the resulting material will be opaque. Further, the material can not thereby be strengthened, whereby it is impossible to obtain a material having adequate durability such as mechanical strength, dimensional stability, solvent resistance and boiling resistance.

From such a viewpoint, it is necessary to use as the component (b) a monomer having a vinyl-type polymerizable group such as an allyl group or a vinyl group, e.g. allyl (meth)acrylate or vinyl (meth)acrylate, in order to ensure satisfactory copolymerization of the polymer (A) with the monomer (B) having a vinyl-type polymerizable group. In a case where a monomer other than the monomer having a vinyl type polymerizable group, such as the monomer (B), and a monomer having a (meth)acryloyl group are used in combination, it is preferred to use as the component (b) a combination of a vinyl-type polymerizable group-containing (meth)acrylate monomer and a (meth)acrylate monomer having at least two (meth)acryloyl groups.

Further, for the copolymerization of the polymer (A) with the monomer (B), etc., a hydrophilic group-containing (meth)acrylate monomer (hereinafter referred to simply as a component (e) may be incorporated as a component for the polymer (A). By using the component (c), the compatibility of the polymer (A) with other hydrophilic monomers will be improved, whereby it is possible to obtain a uniform highly water-absorptive ocular lens material, and a transparent material can more efficiently be obtained without bringing about macro phase-separation.

The component (c) is a hydrophilic group-containing (meth)acrylate monomer having a hydrophilic group selected from the group consisting of an alkoxypolyalkylene glycol residue, an amido group, an N-substituted amido group, an amino group, an N-substitued amino group, a carboxyl group, a hydroxyl group and a polyalkylene glycol residue. Specific examples of the component (c) include an alkoxypolyalkylene glycol mono(meth)acrylate such as methoxydiethylene glycol mono(meth)acrylate, methoxytriethylene glycol mono(meth)acrylate or methoxydipropylene glycol mono(meth)acrylate; (meth)acrylamide; an N-monosubstituted (meth)acrylamide such as N methyl (meth)acrylamide, N-ethyl (meth)acrylamide or N-hydroxyethyl (meth)acrylamide; an N,N-di-substituted (meth)acrylamide such as N,N-dimethyl (meth)acrylamide, N,N-diehtyl (meth)acrylamide or N-ethyl-N-aminoethyl (meth)acrylamide; a (meth)acryloyloxyalkylamine such as (meth)acryloyloxyethylamine; an N-mono-substituted (meth)acryloyloxyalkylamine such as N-methyl (meth)acryloyloxyethylamine; an N,N-di-substituted (meth)acryloyoxyalkylamine such as N,N-dimethyl (meth)acryloyloxyethylamine; (meth)acrylic acid; and a hydroxyl group-containing (meth)acrylate such as hydroxyethyl (meth)acrylate hydroxypropyl (meth)acrylate, hydroxybutyl (meth)acrylate, dihydroxypropyl (meth)acrylate, dihydroxybutyl (meth)acrylate, diethylene glycol mono(meth)acrylate, triethylene glycol mono(meth)acrylate or dipropylene glycol mono(meth)acrylate. These monomers may be used alone or in combination as a mixture of two or more different kinds.

The composition of the polymer (A) i.e. the amount of polymerizable groups or in some cases the amount of hydrophilic groups, may be controlled by adjusting the amounts of the respective components for the preparation of the polymer (A) to be used in the present invention. In the present invention, the polymer (A) is preferably prepared by copolymerizing from 65 to 99.95 mol parts of the component (a), from 0.05 to 5 mol parts of the component (b) and from 0 to 30 mol parts of the component (c), with the total amount of the components (a), (b) and (c) being 100 mol parts, in order to obtain a material having excellent reinforcing effect and transparency.

However, in a case where a hydroxyl group-containing (meth)acrylate such as hydroxyethyl (meth)acrylate or hydroxybutyl (meth)acrylate is used as the component (c), an ester exchange reaction is likely to take place during the polymerization reaction for the preparation, whereby the amount of the (meth)acryloyl group in the polymer (A) tends to increase, and it is not desirable to use such a hydroxyl group-containing (meth)acrylate excessively, and the amount is preferably not higher than 15 mol parts.

The polymer (A) useful for the present invention can efficiently be obtained by copolymerizing the above components (a) and (b) optionally together with the component (c). However, it is necessary to control the polymerization condition so that not all of the polymerizable groups in the component (b) used for introducing the polymerizable groups are subjected to copolymerization (or the cross linking reaction). For this reason, a solution polymeirzation is preferably employed as the polymerization method for the preparation of the polymer (A). As a solvent for the solution polymerization, any solvent may be employed so long as it is capable of dissolving the monomer components and it does not adversely affect the polymerization. As such a solvent, benzene or acetone may be mentioned. These solvents may be used alone or in combination as a mixture of two or more different kinds. The amount of the solvent used varies depending upon the reaction condition, and may be suitably adjusted as the case requires. The reaction temperature and the reaction time are interrelated, and such reaction conditions can not generally be defined. However, the copolymerization reaction is preferably conducted at a relatively low temperature (from 50° to 80° C.) for from a few minutes to a few hours.

For the polymerization, a usual polymerization initiator, such as azobisisobutyronitrile, azobisdimethylvaleronitrile, t-butylhydroperoxide, cumene hydroperoxide or benzoylperoxide, may be employed. The initiator is used usually in an amount of from about 0.001 to about 5 mol parts, preferably from about 0.05 to about 3 mol parts, more preferably from about 0.1 to about 2 mol parts, relative to 100 mol parts of the total amount of all the components used for the preparation of the polymer (A).

The number average molecular weight of the polymer (A) thus prepared, is within a range of from about 5,000 to 200,000. The molecular weight of the polymer (A) affects e.g. the mechanical strength of the highly water-absorptive ocular lens material to be obtained. Namely, the larger the molecular weight, the greater the reniforcing effect of the polymer (A) and the better the mechanical strength of the material thereby obtained. On the other hand, if the molecular weight is too large, it becomes difficult to uniformly mix the polymer (A) with the other monomer when the polymer (A) is to be copolymerized with a hydrophilic monomer such as the monomer (B). For these reasons, the preferred range of the number average molecular weight is from about 10,000 to about 100,000.

The number of polymerizable groups is required to be at least one per molecule of the polymer (A) on an average, to obtain the reniforcing effect of the polymer (A). When the number average molecular weight of the polymer (A) is within a range of from 10,000 to 100,000, the average number of polymerizable groups is preferably from 1 to 5 per molecule of the polymer (A). If the average number of polymerizable groups exceeds this range, it is likely that during the polymerization with a monomer such as the monomer (B), the chemical cross linking density of the resulting material tends to be unnecessarily high, and the water content tends to be low, whereby it becomes difficult to obtain a material having a desirable high water content, or the material tends to be brittle.

In order to attain satisfactory copolymerization of the polymer (A) and the monomer (B) as the main components, the number of free polymerizable groups in the polymer (A) is preferably selected to satisfy the condition of (number of vinyl-type polymerizable groups/number of (meth)acryloyl-type polymerizable groups)≧1.

The polymer (A) to be used in the present invention includes a compound represented by the formula:

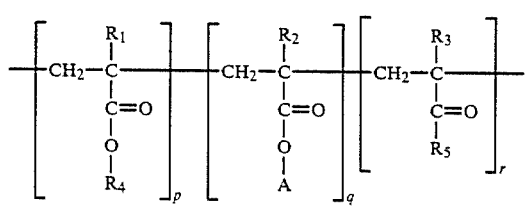

(I)

wherein each of $R_1$, $R_2$ and $R_3$ which may be the same or different, is a hydrogen atom or a methyl group, $R_4$ is an alkyl group, A is a polymerizable group selected from the group consisting of an allyl group, a vinyl group and a (meth)acryloyl group, $R_5$ is a hydrophilic group, and p, q and r are integers satisfying $0.002 \leq q/(p+q+r) \leq 0.05$ and $0 \leq r/(p+q+r) \leq 0.3$, which represent the ratios of the polymerizable groups and the hydrophilic groups.

According to the method described above, the components (a) and (b) are used optionally together with the component (c) for the preparation of the polymer (A) to be used in the present invention. However, the copolymerizable groups may be introduced into the polymer (A) in accordance with the following methods without using the component (b).

(1) The component (a) is copolymerized optionally together with the component (c), with an epoxy group-containing (meth)acrylate such as glycidyl (meth)acrylate, followed by the reaction with a compound having a polymerizable group and being reactive with the epoxy group, such as (meth)acrylic acid or hydroxy styrene, to introduce the polymerizable group.

(2) The component (a) is copolymerized with a hydroxyl group-containing alkyl (meth)acrylate as described as the component (c), followed by the reaction with a desired amount of (meth)acrylic acid chloride to introduce a polymerizable group.

(3) (Meth)acrylic acid is copolymerized with the component (a) optionally together with the component (c), followed by the reaction with a compound having an epoxy group and a polymerizable group, such as glycidyl (meth)acrylate, to introduce the polymerizable group.

The above methods (1) to (3) are all two step reactions. With a view to preparing the polymer (A) useful for the present invention efficiently on an industrial scale, it is most preferred to employ a method wherein the polymer is obtainable in a single step reaction i.e. the above-mentioned method wherein a mixture comprising the components (a) and (b) is copolymerized optionally together with the component (c).

The polymer (A) thus prepared, is colorless and transparent in a state dissolved in a solvent, and is white powder in a dried state.

To obtain a highly water-absorptive ocular lens material of the present invention, the polymer (A) prepared in the above-mentioned manner, is polymerized with the monomer (B) i.e. a fatty acid vinyl ester, the cross linking agent (C), etc.

The monomer (B) is a vinyl ester of a fatty acid. The hydrogen atoms in the fatty acid may be substituted by halogen atoms such as fluorine atoms or chlorine atoms. Specific examples of the monomer (B) include vinyl formate, vinyl acetate, vinyl propionate, vinyl butyrate, vinyl stearate, vinyl monochloroacetate, vinyl trifluoroacetate and vinyl trichloroacetate. These vinyl esters may be used alone or in combination as a mixture of two or more different kinds. When the efficiency for the hydrophilic treatment by saponification is taken into account, it is preferred to employ a lower fatty acid vinyl ester. It is usually preferred to employ vinyl acetate or vinyl trifluoroacetate as a typical material which is readily available.

In the present invention, the polymer (A) and the monomer (B) are used in such proportions that when the total amount of the polymer (A) and the monomer (B) is 100 parts by weight, the polymer (A) is from 2 to 30 parts by weight, preferably from 3 to 20 parts by weight, and the monomer (B) is from 70 to 98 parts by weight, preferably from 80 to 97 parts by weight. If the proportion of the polymer (A) is less than 2 parts by weight, no adequate reinforcing effect of the polymer (A) to the highly water-absorptive ocular lens material of the present invention, can be obtained. On the other hand, if the proportion exceeds 30 parts by weight, it tends to be difficult to maintain the high water content.

For the preparation of the copolymer of the present invention, a part of the monomer (B) may be substituted by any other usual hydrophilic monomer (hereinafter referred to simply as a monomer (D) as the case requires.

Specific examples of the monomer (D) include a polymerizable group-containing lactam such as N-vinyl pyrrolidone or α-methylene-N-methyl pyrrolidone; an alkoxypolyalkylene glycol mono(meth)acrylate such as methoxydiethylene glycol mono(meth)acrylate, methoxytriethylene glycol mono(meth)acrylate or methoxydipropylene glycol mono(meth)acrylate; (meth)acrylamide; an N mono substituted (meth)acrylamide such as N-methyl (meth)acrylamide, N-ethyl (meth)acrylamide or N-hydroxyethyl (meth)acrylamide; an N,N-di-substituted (meth)acrylamide such as N,N-dimethyl (meth)acrylamide, N,N-diethyl (meth)acrylamide or N-ethyl-N-aminoethyl (meth)acrylamide; a (meth)acryloyloxyalkylamine such as (meth)acryloyloxyethylamine; an N-mono-substituted (meth)acryloyloxyalkylamine such a N-methyl (meth)acryloyloxyethylamine; an N,N-di-substituted (meth)acryloyloxy alkylamine such as N,N-dimethyl (meth)acryloyloxyethylamine; (meth)acrylic acid; and a hydroxyl group-containing (meth)acrylate such as hydroxyethyl (meth)acrylate, hydroxypropyl (meth)acrylate, hydroxybutyl (meth)acrylate, dihydroxypropyl (meth)acrylate, dihydroxybutyl (meth)acrylate, diethylene glycol mono(meth)acrylate, triethylene glycol mono(meth)acrylate or dipropylene glycol mono(meth)acrylate. These monomers may be used alone or in combination as a mixture of two or more different kinds.

The proportion of the monomer (D) to the monomer (B) is preferably not higher than about 20 parts by weight relative to 100 parts by weight of the total amount of the monomers (B) and (D), in order to maintain the high water content of the material to be obtained. When the monomer (D) is incorporated, the proportion of the polymer (A) to the 100 parts by weight of all the comonomers, should be maintained within a range of from 2 to 30 parts by weight, preferably from 3 to 20 parts by weight, for the above-mentioned reasons.

As the cross linking agent (C) for the present invention, there may preferably be employed, for example, a cross linking agent which (1) has a polymerizable group readily copolymerizable with other copolymerizable component including a fatty acid vinyl ester such as a vinyl group or an allyl group, (2) has a structure not readily hydrolyzable by saponification for hydrophilic treatment and (3) is readily soluble in and can uniformly be mixed with other copolymerizable component such as a fatty acid vinyl ester. If the cross linking agent (C) is the one which has only a polymerizable group having poor copolymerizability, or which has a structure hydrolyzable by saponification, it is difficult to improve the physical properties such as the mechanical strength, or to minimize elution of substances. Further, if the cross linking agent (C) is not uniformly dissolved in the copolymerizable components, not only a homogeneous material can not be obtained but also a transparent material can not be obtained. The cross linking agent (C) having such properties, includes, for example, a compound having the formula:

$$R_6(O(CH_2)_a)_bO—R_7 \quad (II)$$

wherein each of $R_6$ and $R_7$ which may be the same or different, is $—CH=CH_2$ or $—CH_2—CH=CH_2$ and each of a and b is an integer of from 0 to 5, provided that when a is 0, b is 0; or a compound having the formula:

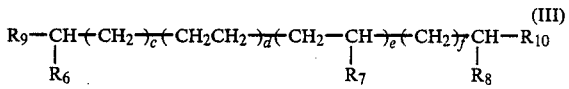
(III)

wherein $R_6$ and $R_7$ are as defined above, $R_8$ is $—CH=CH_2$ or $—CH_2—CH=CH_2$, each of $R_9$ and $R_{10}$ which may be the same or different, is a hydrogen atom, $—CH_3$, $—(CH_2)_gOH$ wherein g is an integer of from 1 to 5, $(CH_2CH_2O)_hR_{11}$ wherein $R_{11}$ is a hydrogen atom or $—CH_3$, h is an integer of from 0 to 12 or $—COOR_{11}$ wherein $R_{11}$ is as defined above, c is an integer of from 0 to 3, d is an integer of from 0 to 500, e is an integer of from 0 to 10,000 and f is an integer of from 0 to 3.

Specific examples of the cross linking agent (C) having the formula II include, for example, ethylene glycol diallyl ether, ethylene glycol divinyl ether, ethylene glycol allylvinyl ether, diethylene glycol diallyl ether, diethylene glycol divinyl ether, diethylne glycol allylvinyl ether, triethylene glycol diallyl ether, triethylene glycol divinyl ether, triethylene glycol allylvinyl ether, tetraethylene glycol diallyl ether, tetraethylene glycol divinyl ether, tetraethylene glycol allylvinyl ether, pentaethylene glycol diallyl ether, pentaethylene glycol divinyl ether, pentaethylene glycol allylvinyl ether, diallyl ether, divinyl ether, allyl vinyl ether, propylene glycol diallyl ether, propylene glycol divinyl ether, propylene glycol allylvinyl ether, dipropylene glycol diallyl ether, dipropylene glycol divinyl ether, dipropylene glycol allylvinyl ether, tripropylene glycol diallyl ether, tripropylene glycol divinyl ether, tripropylene glycol allylvinyl ether, tetrapropylene glycol diallyl ether, tetrapropylene glycol divinyl ether, tetrapropylene glycol allylvinyl ether, butylene glycol diallyl ether, butylene glycol divinyl ether, butylene glycol allylvinyl ether, dibutylene glycol diallyl ether, dibutylene glycol divinyl ether, dibutylene glycol allylvinyl ether, tributylene glycol diallyl ether, tributylene glycol divinyl ether, tributylene glycol allylvinyl ether, tetrabutylene glycol diallyl ether, tetrabutylene glycol divinyl ether, and tetrabutylene glycol allylvinyl ether. Further, specific examples of the cross linking agent (C) of the formula III include, for example, NISSO-PB B series and NISSO-PB G series (which are manufactured by Nippon Soda Kabushiki Kaisha).

The amount of the above-mentioned cross linking agent (C) is from about 0.02 to about 3.0 parts by weight, preferably from 0.05 to 1.0 part by weight based on the total amount of the polymer (A) and the monomer (B) being 100 parts by weight. If the amount of the cross linking agent (C) is less than 0.02 parts by weight, the elution of substances tends to increase, and if the amount exceeds 3.0 parts by weight, the water content tends to decrease or the polymerization tends to be hardly proceed.

The copolymer components (ocular lens components) and their amounts are suitably adjusted for copolymerization depending upon the particular purpose of the desired ocular lenses such as contact lenses or intraocular lenses.

The ocular lens material of the present invention may be prepared, for example, by a process which comprises mixing the polymer (A), the monomer (B), the cross linking agent (C) and/or other optional monomers (the monomer (D) and the like), and polymerizing the mixture by an addition of a polymerization initiator such as a radical copolymerization initiator or a photo polymerization initiator. As specific examples of such a process, there may be mentioned, for example, a method wherein a radical polymerization initiator is mixed with the copolymer components, the mixture is heated, for example, at a temperature of from 40° to 50° C. for from a few hours to a few tens hours for polymerization and then the temperature is gradually raised to 120° C. over a period of ten or more hours to complete the polymerization (heat polymerization), a method wherein a photo polymerization initiator is mixed with the copolymer components, then, and a light having a wave length corresponding to the absorption band for activating the photo polymerization initiator (e.g. ultraviolet rays) is irradiated to the mixture (photo polymerization), or a combination of the heat polymerization and photo polymerization.

When the heat polymerization is employed, the mixture may be heated in a constant temperature bath or in a constant temperature room, or by irradiation of an electromagnetic wave such as a micro wave. The heating may be conducted stepwise. Further, when the photo polymeirzation is employed, a sensitizer may further be added.

For the preparation of the copolymer as the ocular lens material of the present invention, a usual bulk polymerization method is preferably employed to obtain the material at high production efficiency. If necessary, a solution polymerization method may be employed.

Specific examples of the radical polymerization initiator include, for example, azobisisobutylonitrile, azobisdimethylvaleronitrile, benzoyl peroxide, tertbutylhydro peroxide and cumene peroxide.

Specific examples of the photo polymerization initiator include, for example, a benzoyl type photo polymerization initiator such as benzoin, methyl-o-benzoyl benzoate, methyl-o-benzoyl benzoate, methylbenzoyl formate, benzoin methyl ether, benzoin ethyl ether, benzoin isopropyl ether, benzoin isobutyl ether or benzoin-n-butyl ether, a phenone type photo polymerization initiator such as 2-hydroxy-2-methyl-1-phenylpropan-1-one, p-isopropyl-$\alpha$-hydroxyisobutyrophenone, p-tert-butyltrichloroacetophenone, 2,2-dimethoxy-2-phenylacetophenone, $\alpha,\alpha$-dichloro-4-phenoxyacetophenone or N,N,N,N-tetraethyl-4,4-diaminobenzophenone, 1-hydroxycyclohexyl phenyl ketone, 1-phenyl-1,2-propanedione-2-(o-ethoxycarbonyl)oxime, a thioxanethone type photo polymerization initiator such as 2-chlorothioxanethone or 2-methylthioxanethone, dibenzosuberone, 2-ethylanthraquinone, benzophenone acrylate, benzophenone and benzyl.

One or more the radical polymerization initiators or photo polymerization initiators may suitably selected for use from these examples. The amount of the polymerization initiator is suitably within a range of from about 0.001 to 5 parts by weight, preferably from about 0.01 to about 2 parts by weight, more preferably from about 0.02 to 1 part by weight, relative to 100 parts by weight of the total amount of the copolymer components.

For the shaping of ocular lenses such as contact lenses or intraocular lenses, shaping methods commonly used by those skilled in the art may be employed. As such shaping methods, there may be mentioned, for example, mechanical processing such as cutting, grinding or polishing, a molding method by means of a mold and a combination of the molding method and the mechanical processing.

The mechanical processing is a method in which the copolymer components are copolymerized in a suitable mold or vessel to obtain a rod-, block- or plate-shaped copolymer, and then, the mechanical processing such as cutting, grinding or polishing is applied to the copolymer to shape it into a desired ocular lens.

In the molding method, a mold (casting mold) corresponding to the shape of a desired ocular lens is prepared, and the copolymer components are copolymerized in the mold to obtain a shaped product (ocular lens). If necessary, the shaped product thus obtained may be subjected to mechanical finishing treatment. In the combination of the molding method and the mechanical processing, a mold (casting mold) corresponding to one surface of a desired ocular lens, is firstly prepared, and the copolymer components are compolymerized in the mold. Then, the mechanical processing is applied to form the other surface of the ocular lens to obtain a shaped product (ocular lens).

When the mechanical processing is employed, the shaping into an ocular lens is conducted prior to the below-mentioned hydrophilic treatment, since the mechanical processing can not be applied after the hydrophilic treatment.

As compared with the mechanical processing, the molding method or the combination of the molding method and the mechanical processing has advantages such that the starting material components may be in small amounts, the number of process steps may be small, and further, the time required for polymerization is short.

The copolymer obtained by the copolymerization reaction, is then subjected to saponification for hydrophilic treatment, to obtain a highly water-absorptive ocular lens material.

Here, the saponification means treatment of the units derived from the fatty acid vinyl ester in the copolymer, with an alkaline or acidic compound in accordance with a conventional saponification method for a polyvinyl ester to convert the units into an alcohol.

However, the saponification with an acidic compound is slow, and it is thereby rather difficult to obtain a homogeneous product, and it has a further drawback that the side reaction takes place. Therefore, the saponification with an alkaline compound is preferred.

The alkaline compound useful for the saponification is a hydroxide of ammonia, an alkali metal or an alkaline earth metal. Specific examples of such an alkaline compound include ammonium hydroxide, sodium hydroxide, potassium hydroxide and calcium hydroxide. These alkaline compounds are usually solid. Therefore, they may be usually dissolved in alcohols or ethers so that they are used for the saponification reaction in the form of alkaline solutions.

The alcohols include methanol, ethanol, propyl alcohol and butyl alcohol. The ethers include diethyl ether and tetrahydrofuran.

The saponification is conducted by immersing the above-mentioned copolymer in the alkaline solution.

The reaction temperature for the saponification is usually within a range of from 0° to 100° C., preferably from 10° to 60° C. If necessary, the reaction may be conducted at a temperature outside the above temperature range. The reaction time for the saponification varies depending upon the type of the alkaline compound, the concentration of the alkaline compound and the reaction temperature for the saponification, and can not generally be defined. For the practical operation, however, the type and the concentration of the alkaline compound are preferably selected so that the saponification reaction can be completed at room temperature in a few hours. Further, the saponification reaction can be conducted in the hetrogeneous system.

In the case of a copolymer wherein a readily saponifiable fatty acid vinyl ester such as vinyl formate, vinyl monochloroacetate, vinyl trifluoroacetate or vinyl trichloroacetate is used, the saponification can be conducted under a relatively mild condition, and it is possible to selectively saponify the units derived from such a fatty acid vinyl esther without decomposing other ester bonds in the copolymer.

Namely, for instance, when vinyl acetate is to be saponified, it is common to conduct the saponification by using a relatively strong alkaline solution such as a methanol solution of sodium hydroxide. Whereas, when vinyl trifluoroacetate is to be saponified the saponification can be conducted with a relatively weak alkaline solution such as a methanol solution of ammonium hydroxide.

The copolymer thus saponified is then subjected to boiling treatment in a physiological sodium chloride aqueous solution (a 0.9% sodium chloride aqueous solution) for a few hours to obtain a swelled highly water-absorptive ocular lens material which is safe to living bodies.

Now, the highly water-absorptive ocular lens material of the present invention will be described in further detail with reference to Examples. However, it should be understood that the present invention is by no means restricted to such specific Examples.

REFERENCE EXAMPLE 1

Preparation of a (meth)acrylate polymer having at least one polymerizable group per molecule on an average (polymer (A))

Into a three-necked round bottom flask, 95 g of methyl methacrylate, 1.80 g of allyl methacrylate, 0.64 g of azobisisobutyronitrile as a polymerization initiator and 720 ml of benzene as a solvent, were added and polymerized under stirring at a refluxing temperature for 2 hours. Then, the polymerization solution thus obtained was poured into n-hexane, and the copolymer precipitated was collected and dried under reduced pressure. The copolymer was dissolved in benzene, and then poured into a large amount of n-hexane, whereby it was again precipitated for purification. The precipitates were collected and dried under reduced pressure to obtain a polymer (A).

The number average molecular weight, the molecular weight distribution and the average number of polymerizable groups per molecule of the polymer (A) thus obtained, were measured in accordance with the following methods. The results are shown in Table 1 together with the yield.

Number average molecular weight
  Measured by gel permeation chromatography.
Molecular weight distribution
  The weight average molecular weight ($\overline{Mw}$) was measured in the same manner as in the case of the above number average molecular weight ($\overline{Mn}$), and the molecular weight distribution was calculated in accordance with the following equation.

$$\text{Molecular weight distribution} = \overline{Mw}/\overline{Mn}$$

Average number of polmerizable groups per molecule
  Measured by gel permeation chromatography and Fourier's conversion proton nuclear magnetic resonance spectroscopy.

REFERENCE EXAMPLES 2 to 5

In the same manner as in Reference Example 1, various polymers (A) were prepared with the components and the proportions as identified in Table 1.

The number average molecular weight, the molecular weight distribution and the average number of polymerizable groups per molecule of each polymer (A) thus prepared were measured in the same manner as in Reference Example 1. The results are shown in Table 1 together with the yield.

TABLE 1

| | Components (parts by weight) | | | | | Physical properties | | | |
| --- | --- | --- | --- | --- | --- | --- | --- | --- | --- |
| | | | | | | Number average molecular weight (Mn) | Molecular weight distribution | Average number of polymerizable groups *1 | |
| Reference Example | Component (a) | Component (b) | Component (c) | Polymerization initiator | Yeild (%) | | | Acryloyl group | Methacryloyl group |
| 1 | MMA 99.01 | AMA 0.99 | — | AIBN 0.35 | 64 | $1.9 \times 10^4$ | 1.9 | 1.6 | — |
| 2 | MMA 98.76 | AMA 1.24 | — | AIBN 0.35 | 66 | $2.0 \times 10^4$ | 1.9 | 2.1 | — |
| 3 | MMA 98.52 | AMA 1.48 | — | AIBN 0.35 | 64 | $2.0 \times 10^4$ | 1.9 | 2.5 | — |
| 4 | NMA 95.82 | AMA 0.74 EDMA 0.25 | — | AIBN 0.83 | 40 | $3.1 \times 10^4$ | 2.1 | 1.2 | 1.1 |
| 5 | NMA | AMA | HEMA | AIBN | 35 | $2.8 \times 10^4$ | 2.8 | 1.4 | — |

TABLE 1-continued

| Reference Example | Components (parts by weight) | | | | Yeild (%) | Physical properties | | | |
|---|---|---|---|---|---|---|---|---|---|
| | Component (a) | Component (b) | Component (c) | Polymerization initiator | | Number average molecular weight (Mn) | Molecular weight distribution | Average number of polymerizable groups *1 | |
| | | | | | | | | Acryloyl group | Methacryloyl group |
| | 95.39 | 0.75 | 3.86 | 0.82 | | | | | |

(Note)
NMA: Methyl methacrylate
AMA: Allyl methacrylate
AIBN: Azobisisobutyronitrile
EDMA: Ethylene glycol dimethacrylate
HEMA: Hydroxyethyl methacrylate
*1: Average number of polymerizable groups per molecule of the polymers (A) ([Acryloyl group] + [Methacryloyl groups] ≧ 1)

EXAMPLE 1

Into a 100 ml Erlenmeyer flask, 6.0 g (10 parts by weight) of the polymer (A) obtained in Reference Example 2 was charged, and 0.14 g (0.2 part by weight) of a cross linking agent and 54 g (90 parts by weight) of a fatty acid vinyl ester were added thereto and completely dissolved to bring the composition as shown in Table 2. 0.042 g (0.07 part by weight) of a polymerization initiator was added thereto and dissolved. The solution was transferred to a glass test tube having an inner diameter of 14 mm. Then, a polyethylene stopper was placed on the test tube, and the polymerization was conducted in a constant temperature bath at 35° C. for 36 hours. Then, the temperature was raised to 50° C., and the polymerization was conducted for 8 hours. The product was transferred to a circulating drier. Here, the product was heated at 50° C. for 5 hours, and then heated for 9 hours while gradually raising the temperature from 60° C. to 110° C., to complete the polymerization. The product was cooled to room temperature and then heated at 100° C. for 2 hours to remove the distortion.

10 pieces of a film having a thickness of 0.14 mm and a diameter of 11.6 mm and 5 pieces of a plate having a thickness of 0.5 mm and a diameter of 11.6 mm were prepared by cutting the rod-shaped material thereby obtained.

Then, into a Petri dish having a diameter of about 10 cm, about 50 ml of a methanol solution of 0.25 N sodium hydroxide was introduced. The films and the plates were immersed therein and left to stand for two hours to complete saponification. After washing then with water, the films and plates and 500 ml of water were introduced to a 1 l Erlenmeyer flask, and boiled for 24 hours. After cooling, 500 ml of water was replaced by 500 ml of a physiological sodium chloride aqueous solution, and the boiling was conducted for 2 hours. Then, the physiological sodium chloride solution was replaced by water.

With respect to the test specimens thus treated for saponification and elution, various physical properties were measured in accordance with the following methods. The results are shown in Table 2.

Outer appearance upon absorption of water

The outer appearance of a test specimen upon absorption of water to the equilibrium state was visually evaluated.

Water content:

The water content of a test specimen (thickness on cutting: 0.5 mm) was determined in accordance with the following equation.

Water content (%) = $W - W_0/W \times 100$ where W is the weight (g) of the test specimen upon absorption of water to the equilibrium state, and $W_0$ is the weight (g) of the test specimen in a dried state.

Boiling resistance:

A test specimen was boiled in a physiological sodium chloride aqueous solution for about 2 hours and observed to see if it was dissolved.

Solvent resistance

A test specimen was immersed in a dimethyl slufoxide solvent and heated to 80° C., and observed to see if it was dissolved.

Refractive index

The refractive index ($n_D^{20}$) of a test specimen having a thickness of about 0.2 mm (thickness on cutting: 0.14 mm) upon absorption of water to the equilibrium state, was determined by using Erma new model Abbe's refractometer manufactured by Erma Optical Works, Ltd.

Oxygen permeation coefficient

The oxygen permeation coefficient of the test specimen having a thickness of about 0.2 mm (thickness on cutting: 0.14 mm) upon absorption of water to the equilibrium state was determined in a physiological sodium chloride aqueous solution at 35° C. by using Seikaken type film oxygen permeation measuring instrument manufactured by Rikaseiki Kogyo Kabushiki Kaisha.

Penetration resistance:

By means of an Instron type compression tester, a pressing needle having a diameter of 1/16 inch was pressed against the center of the test specimen having a thickness of about 0.2 mm (thickness on cutting: 0.14 mm) upon absorption of water to the equilibrium state, and the load (g) at the time of the breakage of the test specimen was measured.

Elongation:

The elongation (%) at the time of the breakage of the test specimen in the above-mentioned measurement of the penetration resistance (g), was measured.

Strength index:

The mechanical strength of the material depends on both the elongation (%) and the penetration resistance (g). Therefore, as an index for relative strength, the strength index was calculated in accordance with the following equation.

$$\text{Strength index} = \frac{\text{Penetration resistance (g)} \times \text{Elongation (\%)}}{2 \times \text{Film thickness } (\mu m)}$$

Difference in the amount of consumption of potassium permanganate:

The measurement was conducted in accordance with the elution test stipulated by the Ministry of Health and Welfare in Japan.

EXAMPLES 2 to 21

To bring the composition as shown in Table 2, the components were mixed in the same manner as in Example 1 and polymerized. Test specimens were cut out, and subjected to saponification and elution treatments. Then, various physical properties of the test specimens were measured in the same manner as in Example 1. The results are shown in Table 2.

TABLE 2

| | | Example No. 1 | Example No. 2 | Example No. 3 |
|---|---|---|---|---|
| Components (parts by weight) | Monomer (B) | VAc 90 | VAc 90 | VAc 90 |
| | Polymer (A) | Reference Example 2 10 | Reference Example 5 10 | Reference Example 1 10 |
| | Cross linking agent (C) | NISSO B 0.2 | NISSO G 0.2 | TRIAM 0.2 |
| | Polymerization initiator | V-65 0.07 | V-65 0.07 | V-65 0.07 |
| Physical properties | Outer appearance upon absorption of water | Transparent and colorless | Transparent and colorless | Transparent and colorless |
| | Water content (%) | 77.1 | 77.4 | 76.7 |
| | Boiling resistance | Not dissolved | Not dissolved | Not dissolved |
| | Solvent resistance | Not dissolved | Not dissolved | Not dissolved |
| | Refractive index ($n_D^{20}$) | 1.363 | 1.363 | 1.364 |
| | Oxygen permeation coefficient *1 | 38.8 | 38.4 | 42.8 |
| | Penetration resistance (g) | 418 | 412 | 429 |
| | Elongation (%) | 187 | 181 | 188 |
| | Strength index (g · %/μm) | 196 | 186 | 201 |
| | Difference in the amount of the consumption of KMnO$_4$ (ml) | 1.74 | 1.79 | 1.05 |

| | | Example No. 4 | Example No. 5 | Example No. 6 |
|---|---|---|---|---|
| Components (parts by weight) | Monomer (B) | VAc 90 | VAc 90 | VAc 90 |
| | Polymer (A) | Reference Example 2 10 | Reference Example 2 10 | Reference Example 4 10 |
| | Cross linking agent (C) | TRIAM 0.1 | TRIAM 0.15 | TRIAM 0.2 |
| | Polymerization initiator | V-65 0.07 | V-65 0.07 | V-65 0.07 |
| Physical properties | Outer appearance upon absorption of water | Transparent and colorless | Transparent and colorless | Transparent and colorless |
| | Water content (%) | 77.4 | 76.7 | 76.4 |
| | Boiling resistance | Not dissolved | Not dissolved | Not dissolved |
| | Solvent resistance | Not dissolved | Not dissolved | Not dissolved |
| | Refractive index ($n_D^{20}$) | 1.368 | 1.369 | 1.370 |
| | Oxygen permeation coefficient *1 | 40.7 | 42.6 | 39.1 |
| | Penetration resistance (g) | 402 | 445 | 475 |
| | Elongation (%) | 206 | 211 | 215 |
| | Strength index (g · %/μm) | 208 | 235 | 256 |
| | Difference in the amount of the consumption of KMnO$_4$ (ml) | 1.66 | 1.37 | 1.14 |

| | | Example No. 7 | Example No. 8 | Example No. 9 |
|---|---|---|---|---|
| Components (parts by weight) | Monomer (B) | VAc 90 | VAc 88 | VAc 93.5 |
| | Polymer (A) | Reference Example 2 10 | Reference Example 2 12 | Reference Example 3 6.5 |
| | Cross linking agent (C) | TRIAM 0.3 | TRIAM 0.15 | TRIAM 0.5 |
| | Polymerization initiator | V-65 0.07 | V-65 0.07 | V-65 0.07 |
| Physical properties | Outer appearance upon absorption of water | Transparent and | Transparent and | Transparent and |

TABLE 2-continued

| | | | | |
|---|---|---|---|---|
| | | colorless | colorless | colorless |
| | Water content (%) | 75.6 | 74.4 | 77.9 |
| | Boiling resistance | Not dissolved | Not dissolved | Not dissolved |
| | Solvent resistance | Not dissolved | Not dissolved | Not dissolved |
| | Refractive index ($n_D^{20}$) | 1.371 | 1.373 | 1.366 |
| | Oxygen permeation coefficient *1 | 38.8 | 37.2 | 41.6 |
| | Penetration resistance (g) | 481 | 494 | 394 |
| | Elongation (%) | 196 | 178 | 219 |
| | Strength index (g · %/μm) | 235 | 220 | 217 |
| | Difference in the amount of the consumption of $KMnO_4$ (ml) | 1.04 | 1.41 | 0.53 |

| | | Example No. | | |
|---|---|---|---|---|
| | | 10 | 11 | 12 |
| Components (parts by weight) | Monomer (B) | VAc 93 | VAc 92 | VAc 93 |
| | Polymer (A) | Reference Example 3 7 | Reference Example 2 8 | Reference Example 1 7 |
| | Cross linking agent (C) | TRIAM 0.2 | TRIAM 0.2 | TRIAM 0.3 |
| | Polymerization initiator | V-65 0.07 | V-65 0.07 | V-65 0.07 |
| Physical properties | Outer appearance upon absorption of water | Transparent and colorless | Transparent and colorless | Transparent and colorless |
| | Water content (%) | 79.9 | 78.5 | 79.2 |
| | Boiling resistance | Not dissolved | Not dissolved | Not dissolved |
| | Solvent resistance | Not dissolved | Not dissolved | Not dissolved |
| | Refractive index ($n_D^{20}$) | 1.362 | 1.365 | 1.364 |
| | Oxygen permeation coefficient *1 | 49.1 | 45.7 | 46.7 |
| | Penetration resistance (g) | 418 | 451 | 377 |
| | Elongation (%) | 260 | 253 | 242 |
| | Strength index (g · %/μm) | 273 | 286 | 230 |
| | Difference in the amount of the consumption of $KMnO_4$ (ml) | 1.56 | 1.27 | 1.47 |

| | | Example No. | | |
|---|---|---|---|---|
| | | 13 | 14 | 15 |
| Components (parts by weight) | Monomer (B) | VAc 93.5 | VAc 93 | VAc 93 |
| | Polymer (A) | Reference Example 2 6.5 | Reference Example 5 7 | Reference Example 4 7 |
| | Cross linking agent (C) | TRIAM 0.4 | TRIAM 0.2 | TRIAM 0.3 |
| | Polymerization initiator | V-65 0.07 | V-65 0.07 | V-65 0.07 |
| Physical properties | Outer appearance upon absorption of water | Transparent and colorless | Transparent and colorless | Transparent and colorless |
| | Water content (%) | 78.9 | 80.3 | 79.5 |
| | Boiling resistance | Not dissolved | Not dissolved | Not dissolved |
| | Solvent resistance | Not dissolved | Not dissolved | Not dissolved |
| | Refractive index ($n_D^{20}$) | 1.364 | 1.363 | 1.365 |
| | Oxygen permeation coefficient *1 | 44.9 | 45.4 | 46.0 |
| | Penetration resistance (g) | 452 | 346 | 338 |
| | Elongation (%) | 264 | 240 | 221 |
| | Strength index (g · %/μm) | 301 | 208 | 187 |
| | Difference in the amount of the consumption of $KMnO_4$ (ml) | 0.92 | 1.46 | 1.17 |

| | | Example No. | | |
|---|---|---|---|---|
| | | 16 | 17 | 18 |
| Components (parts by weight) | Monomer (B) | VAc 93.5 | VAc 93.5 | VAc 93.5 |
| | Polymer (A) | Reference | Reference | Reference |

TABLE 2-continued

|  |  | Example 2 | Example 2 | Example 2 |
|---|---|---|---|---|
|  |  | 6.5 | 6.5 | 6.5 |
|  | Cross linking agent (C) | TRIAM | TRIAM | TRIAM |
|  |  | 0.2 | 0.25 | 0.3 |
|  | Polymerization initiator | V-65 | V-65 | V-65 |
|  |  | 0.07 | 0.07 | 0.07 |
| Physical properties | Outer appearance upon absorption of water | Transparent and colorless | Transparent and colorless | Transparent and colorless |
|  | Water content (%) | 80.8 | 80.4 | 79.9 |
|  | Boiling resistance | Not dissolved | Not dissolved | Not dissolved |
|  | Solvent resistence | Not dissolved | Not dissolved | Not dissolved |
|  | Refractive index ($n_D^{20}$) | 1.363 | 1.363 | 1.364 |
|  | Oxygen permeation coefficient *1 | 47.9 | 47.7 | 47.2 |
|  | Penetration resistance (g) | 312 | 302 | 310 |
|  | Elongation (%) | 242 | 230 | 218 |
|  | Strength index (g · %/μm) | 189 | 174 | 169 |
|  | Difference in the amount of the consumption of KMnO$_4$ (ml) | 1.55 | 1.29 | 1.14 |

|  |  | Example No. | | |
|---|---|---|---|---|
|  |  | 19 | 20 | 21 |
| Components (parts by weight) | Monomer (B) | VAc | VAc | VAc |
|  |  | 92.5 | 93 | 93.75 |
|  | Polymer (A) | Reference Example 2 | Reference Example 2 | Reference Example 2 |
|  |  | 7.5 | 7 | 6.25 |
|  | Cross linking agent (C) | TRIAM | TRIAM | TRIAM |
|  |  | 0.2 | 0.25 | 0.4 |
|  | Polymerization initiator | V-65 | V-65 | V-65 |
|  |  | 0.07 | 0.07 | 0.07 |
| Physical properties | Outer appearance upon absorption of water | Transparent and colorless | Transparent and colorless | Transparent and colorless |
|  | Water content (%) | 79.8 | 80.0 | 79.5 |
|  | Boiling resistance | Not dissolved | Not dissolved | Not dissolved |
|  | Solvent resistance | Not dissolved | Not dissolved | Not dissolved |
|  | Refractive index ($n_D^{20}$) | 1.364 | 1.364 | 1.365 |
|  | Oxygen permeation coefficient *1 | 48.4 | 46.6 | 44.3 |
|  | Penetration resistance (g) | 316 | 301 | 321 |
|  | Elongation (%) | 218 | 219 | 216 |
|  | Strength index (g · %/μm) | 172 | 165 | 174 |
|  | Difference in the amount of the consumption of KMnO$_4$ (ml) | 1.24 | 1.25 | 0.85 |

*1 $\left(\left(\dfrac{ml(STP) \cdot cm^2}{cm^3 \cdot sec \cdot mmHg}\right) \times 10^{11}\right)$ (Note)
VAc: Vinyl acetate
NISSO B: tradename: NISSO PB-B, manufactured by Nippon Soda Kabushiki Kaisha (A compound having the formula III wherein each of $R_9$ and $R_{10}$ is a hydrogen atom, each of $R_6$, $R_7$ and $R_8$ is —CH=CH$_2$, c is 1, d is 0, e is 1,000 and f is 1)
NISSO G: tradename: NISSO PB-G, manufactured by Nippon Soda Kabushiki Kaisha (A compound having the formula III wherein each of $R_9$ and $R_{10}$ is $\text{+CH}_2\text{+}_2\text{OH}$, each of $R_6$, $R_7$ and $R_8$ is —CH=CH$_2$, c is 1, d is 0, e is 1,000 and f is 1)
TRIAM: Diethylene glycol diallyl ether, tradename: TRIAM 501, manufactured by Wako Junyaku Kogyo Kabushiki Kaisha (A compond having the formula II wherein each of $R_6$ and $R_7$ is —CH$_2$—CH=CH$_2$, b is 2 and a is 2)
V-65: Azobisdimethylvaleronitrile

COMPARATIVE EXAMPLES 1 to 9

To bring the composition as shown in Table 3, the respective components were mixed in the same manner as in Examples 1 to 21 and polymerized, test specimens were cut out and subjected to saponification and elution treatment. Then, various physiological properties of the test specimens were measured in the same manner as in Examples 1 to 21. The results are shown in Table 3.

TABLE 3

|  |  | Example No. | | |
|---|---|---|---|---|
|  |  | 1 | 2 | 3 |
| Components (parts by | Monomer (B) | VAc | VAc | VAc |
|  |  | 90 | 90 | 90 |

TABLE 3-continued

| weight | Polymer (A) | Reference Example 2 10 | Reference Example 2 10 | Reference Example 2 10 |
|---|---|---|---|---|
| | Cross linking agent (C) | — | AADA 0.1 | AADA 0.2 |
| | Polymerization initiator | V-65 0.07 | V-65 0.07 | V-65 0.07 |
| Physical properties | Outer appearance upon absorption of water | Transparent and colorless | Transparent and colorless | Transparent and colorless |
| | Water content (%) | 79.1 | 79.0 | 78.9 |
| | Boiling resistance | Not dissolved | Not dissolved | Not dissolved |
| | Solvent resistance | Not dissolved | Not dissolved | Not dissolved |
| | Refractive index ($n_D^{20}$) | 1.358 | 1.358 | 1.359 |
| | Oxygen permeation coefficient *1 | 43.8 | 42.5 | 41.2 |
| | Penetration resistance (g) | 300 | 315 | 319 |
| | Elongation (%) | 196 | 202 | 200 |
| | Strength index (g · %/μm) | 148 | 160 | 159 |
| | Difference in the amount of the consumption of KMnO$_4$ (ml) | 3.36 | 3.31 | 3.23 |

| | | Example No. | | |
|---|---|---|---|---|
| | | 4 | 5 | 6 |
| Components (parts by weight) | Monomer (B) | VAc 90 | VAc 90 | VAc 90 |
| | Polymer (A) | Reference Example 2 10 | Reference Example 2 10 | Reference Example 2 10 |
| | Cross linking agent (C) | AADA 0.3 | AMA 0.2 | SADA 0.2 |
| | Polymerization initiator | V-65 0.07 | V-65 0.07 | V-65 0.07 |
| Physical properties | Outer appearance upon absorption of water | Transparent and colorless | Transparent and colorless | Transparent and colorless |
| | Water content (%) | 78.7 | 78.9 | 79.4 |
| | Boiling resistance | Not dissolved | Not dissolved | Not dissolved |
| | Solvent resistance | Not dissolved | Not dissolved | Not dissolved |
| | Refractive index ($n_D^{20}$) | 1.359 | 1.363 | 1.362 |
| | Oxygen permeation coefficient *1 | 43.1 | 44.5 | 46.8 |
| | Penetration resistance (g) | 328 | 405 | 386 |
| | Elongation (%) | 199 | 222 | 223 |
| | Strength index (g · %/μm) | 164 | 226 | 215 |
| | Difference in the amount of the consumption of KMnO$_4$ (ml) | 3.42 | 4.54 | 4.46 |

| | | Example No. | | |
|---|---|---|---|---|
| | | 7 | 8 | 9 |
| Components (parts by weight) | Monomer (B) | VAc 90 | VAc 90 | VAc 90 |
| | Polymer (A) | Reference Example 2 10 | Reference Example 2 10 | Reference Example 2 10 |
| | Cross linking agent (C) | CATA 0.2 | MADA 0.2 | DBAC 0.2 |
| | Polymerization initiator | V-65 0.07 | V-65 0.07 | V-65 0.07 |
| Physical properties | Outer appearance upon absorption of water | Transparent and colorless | Transparent and colorless | Transparent and colorless |
| | Water content (%) | 78.8 | 79.0 | 79.5 |
| | Boiling resistance | Not dissolved | Not dissolved | Not dissolved |
| | Solvent resistance | Not dissolved | Not dissolved | Not dissolved |
| | Refractive index ($n_D^{20}$) | 1.364 | 1.363 | 1.359 |
| | Oxygen permeation coefficient *1 | 43.5 | 44.9 | 46.6 |
| | Penetration resistance (g) | 439 | 430 | 333 |
| | Elongation (%) | 226 | 225 | 210 |
| | Strength index (g · %/μm) | 247 | 242 | 175 |

TABLE 3-continued

| | | | |
|---|---|---|---|
| Difference in the amount of the consumption of KMnO₄ (ml) | 4.19 | 4.10 | 3.74 |

(Note)

*1 $\left(\left(\dfrac{ml(STP) \cdot cm^2}{cm^3 \cdot sec \cdot mmHg}\right) \times 10^{11}\right)$ AADA: Diallyl adipate
AMA: Allyl methacrylate
SADA: Diallyl succinate
CATA: Triallyl cyanulate
MADA: Diallyl maleate
DBAC: Diethylene glycol bisallylcarbonate The above results show that in Examples 1 to 21 of the present invention, the differences in the amount of consumption of potassium permanganate were at most 2.0 ml whereas those in Comparative Examples 1 to 9 were at least 3.0 ml.

Thus, it is evident that the amount of the eluted substances is small with the materials obtained in Examples 1 to 21 of the present invention, as compared with the materials obtained in Comparative Examples 1 to 9.

Further, it is evident that the materials obtained in Examples 1 to 21 of the present invention are superior to the material obtained in Reference Example 1 using no cross linking agent in the penetration resistance, the elongation and the strength index.

EXAMPLES 22 and 23

A single-faced mold having an outer teflon frame attached to a casting mold having a surface corresponding to the shape of the inner surface of a contact lens was prepared.

7 parts by weight of the polymer (A) obtained in Reference Example 2, 0.5 part by weight of the cross linking agent and 93 parts by weight of a fatty acid vinyl ester were dissolved in the same manner as in Example 1 to obtain the composition as identified in Table 4, and 0.1 part by weight of a photo polymerization initiator was added and dissolved therein to obtain a solution. The solution was injected into the single-faced mold.

Then, the single-faced mold was covered with a glass plate, and the single-faced mold and the glass plate were fixed by a clip.

The mold was transferred to a circulating drier, and an ultraviolet ray was irradiated at 40° C. for 4 hours by an ultrovoilet fluorescense lamp to polymerize the solution. Then, the glass plate and the outer frame were removed, and to shape the outer surface of the contact lens, cutting was applied to the copolymer to obtain a copolymer product having a shape of a contact lens.

Then, the copolymer product was immersed in a methanol solution of 0.25N sodium hydroxide for 2 hours in the same manner as in Example 1 for the saponification treatment, washed with the water and subjected to the boiling treatment to obtain a water-absorptive contact lens.

Various physical properties of the water-absorptive contact lens thereby obtained were measured in the same manner as in Example 1. The results are shown in Table 4.

TABLE 4

| | | Example No. | |
|---|---|---|---|
| | | 22 | 23 |
| Components (parts by weight) | Monomer (B) | VAc 93 | VAc 92 |
| | Polymer (A) | Reference Example 2 7 | Reference Example 2 8 |
| | Cross linking agent (C) | TRIAM 0.5 | TRIAM 0.4 |
| | Polymerization initiator | Drc 0.1 | Drc 0.1 |
| Physical properties | Outer appearance upon absorption of water | Transparent and colorless | Transparent and colorless |
| | Water content (%) | 79.6 | 79.3 |
| | Boiling resistance | Not dissolved | Not dissolved |
| | Solvent resistance | Not dissolved | Not dissolved |
| | Refractive index ($n_D^{20}$) | 1.365 | 1.365 |
| | Oxygen permeation coefficient *1 | 47.1 | 46.5 |
| | Penetration resistance (g) | 368 | 320 |
| | Elongation (%) | 228 | 198 |
| | Strength index (g · %/μm) | 224 | 163 |
| | Difference in the amount of the comsumption of KMnO₄ (ml) | 1.10 | 1.30 |

(Note)

*1 $\left(\left(\dfrac{ml(STP) \cdot cm^2}{cm^3 \cdot sec \cdot mmHg}\right) \times 10^{11}\right)$ Drc: 2-hydroxy-2-methyl-1-phenylpropan-1-one (tradename: Darocur 1173, manufactured by Merk Co., Ltd.)

These results show that the highly water-absorptive ocular lens material shaped into contact lenses by the combination of the molding method and the mechanical processing was not inferior to the materials obtained in Examples 1 to 21 (mechanical processing method) in the physical properties.

The highly water-absorptive ocular lens material of the present invention, contains no substantial amount of a polymer not bonded to the polymer consisting the lens material. Therefore, the amount of the eluted substances is extremely small, and the post treatment such as the boiling treatment of such lens material can be completed in an extremely short period of time. Thus, the lens material of the present invention easily passes the elution test stipulated by the Ministry of Health and Welfare in Japan.

Further, the highly water-absorptive ocular lens material of the present invention has the water content at a high level of from about 70 to about 80%. Therefore, upon absorption of water, the lens material exhibits excellent gas permeability by means of the absorbed water.

Furthermore, the highly water-absorptive ocular lens material of the present invention is reinforced by the polymer (A), and partly chemically cross-linked by the polymer (A), and yet, it is cross-linked by the cross linking agent. Therefore, although the water content of the material is high, it is excellent in the durability such as the demensional stability, the boiling resistance or the solvent resistance and further has improved mechanical strength.

Further, a macro phase separation does not occur in the highly water-absorptive ocular lens material of the present invention, and it is a transparent material and is excellent in the compatibility with a living body. Therefore, it can preferably be used as an ocular lens material which is directly contacted with a living body, such as a contact lens, intraocular lens or artificial cornea.

We claim:

1. A highly water absorptive ocular lens material obtained by saponification for hydrophilic treatment of a copolymer composed essentially of:
   (A) from 2 to 30 parts by weight of a (meth)acrylate polymer having at least one polymerizable group per molecule on an average obtained by copolymerizing (a) an alkyl (meth)acrylate monomer and (b) a monomer having at least two polymerizable groups per molecule, as the main components;
   (B) from 70 to 98% by weight of a fatty acid vinyl ester; and
   (C) from 0.02 to 3.0 parts by weight of a cross linking agent which is a compound of the formula:

$$R_6(O(CH_2)_a)_bO-R_7 \quad (II)$$

wherein each of $R_6$ and $R_7$ which may be the same or different, is $-CH=CH_2$ or $-CH_2-CH=CH_2$, and each of a and b is an integer of from 0 to 5, provided that when a is 0, b is 0; or the formula:

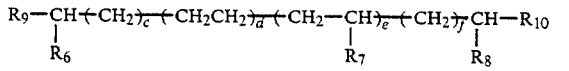

(III)

wherein $R_6$ and $R_7$ are as defined above, $R_8$ is $-CH=CH_2$ or $-CH_2-CH=CH_2$, each of $R_9$ and $R_{10}$ which may be the same or different, is a hydrogen atom, $-CH_3$, $(CH_2)_g-OH$ wherein g is an integer of from 1 to 5, $(CH_2CH_2O)_h R_{11}$ wherein $R_{11}$ is a hydrogen atom or $-CH_3$, and h is an integer of from 0 to 12, or $-COOR_{11}$ wherein $R_{11}$ is as defined above, c is an integer of from 0 to 3, is an integer of from 0 to 500, e is an integer of from 1 to 10,000, and f is an integer of from 0 to 3, provided that the total amount of polymer (A) and monomer (B) is 100 parts by weight.

2. The ocular lens material according to claim 1, wherein the alkyl (meth)acrylate monomer (a) is at least one member selected from the group consisting of methyl (meth)acrylate, ethyl (meth)acrylate, propyl (meth)acrylate, butyl (meth)acrylate, pentyl (meth)acrylate, hexyl (meth) acrylate, dodecyl (meth)acrylate, cyclohexyl (meth)acrylate, trifluoroethyl (meth)acrylate, pentafluoroisopropyl (meth)acrylate and hexafluoroisopropyl (meth) acrylate.

3. The ocular lens material according to claim 1, wherein the monomer (b) is at least one member selected from the group consisting of allyl (meth) acrylate, vinyl (meth)acrylate, ethylene glycol di(meth)acrylate, diethylene glycol di(meth) acrylate, triethylene glycol di(meth)acrylate and dipropylene glycol di(meth)acrylate.

4. The ocular lens material according to claim 1, wherein the (meth)acrylate polymer (A) has (c) a hydrophilic group-containing (meth)acrylate monomer copolymerized with the monomers (a) and (b).

5. The ocular lens material according to claim 4, wherein the (meth)acrylate monomer (c) has a hydrophilic group selected from the group consisting of an alkoxypolyalkylene glycol residue, an amido group, an N-substituted amido group, an amino group, an N-substituted amino group, a carboxyl group, a hydroxyl group and a polyalkylene glycol residue.

6. The ocular lens material according to claim 1, wherein the (meth)acrylate polymer (A) is obtained by copolymerizing from 65 to 99.95 mol parts of the alkyl (meth)acrylate monomer (a), from 0.05 to 5 mol parts of the monomer (b) and from 0 to 30 mol parts of (c) a hydrophilic group-containing (meth)acrylate monomer.

7. The ocular lens material according to claim 1, wherein the (meth)acrylate polymer (A) has a number average molecular weight of from about 5,000 to about 200,000.

8. The ocular lens material according to claim 1, wherein the (meth)acrylate polymer (A) has a number average molecular weight of from 10,000 to 100,000 and contains from 1 to 5 polymerizable groups per molecule on an average.

9. The ocular lens material according to claim 1, wherein the polymer (A) has the formula:

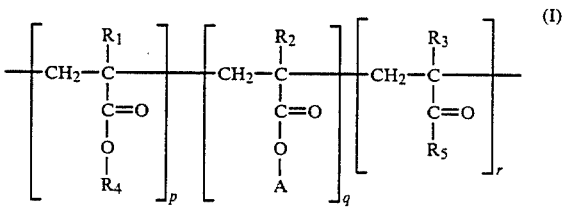

(I)

wherein each of $R_1$, $R_2$ and $R_3$ which may be the same or different, is a hydrogen atom or a methyl group, $R_4$ is an alkyl group, A is a polymerizable group selected from the group consisting of an allyl group, a vinyl group and a (meth)acryloyl group, $R_5$ is a hydrophilic group, and p, q and r are integers satisfying $0.002 \leq q/(p+q+r) \leq 0.05$ and $0 \leq r/(p+q+r) \leq 0.03$.

10. The ocular lens material according to claim 1, wherein the fatty acid vinyl ester (B) is at least one member selected from the group consisting of vinyl formate, vinyl acetate, vinyl propionate, vinyl butyrate, vinyl stearate, vinyl monochloroacetate, vinyl trifluoroacetate and vinyl trichloroacetate.

11. The ocular lens material according to claim 1, wherein a part of the monomer (B) is susbstituted by (D) at least one hydrophilic monomer selected from the group consisting of a polymerizable group-containing lactam, an alkoxypolyalkylene glycol mono(meth)acrylate, a (meth)acrylamide, an N-mono-substituted (meth)acrylamide, an N,N-disubstituted (meth)acrylamide, a (meth)acryloyloxyalkylamine, an N-mono-substituted (meth)acryloyloxyalkylamine, an N,N-disubstituted (meth)acryloyloxy alkylamine, (meth)acrylic acid and a hydroxyl group-containing (meth)acrylate.

12. A contact lens made of the ocular lens material as defined in claim 1.

* * * * *